US00PP37035P2

(12) United States Plant Patent
Rodriguez et al.

(10) Patent No.: US PP37,035 P2
(45) Date of Patent: Oct. 21, 2025

(54) BLACKBERRY PLANT NAMED 'DrisBlackThirtySix'

(50) Latin Name: ***Rubus* L. subgenus *Rubus***
Varietal Denomination: DrisBlackThirtySix

(71) Applicant: Driscoll's, Inc., Watsonville, CA (US)

(72) Inventors: Brando Alvarez Rodriguez, Jalisco (MX); Gavin R. Sills, Gilroy, CA (US); Raymond L. Jacobs, III, Aptos, CA (US); Carmen Marín, Jalisco (MX)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 19/053,014

(22) Filed: Feb. 13, 2025

(51) Int. Cl.
*A01H 5/08* (2018.01)
*A01H 6/74* (2018.01)

(52) U.S. Cl.
USPC ..... Plt./203
CPC ..... *A01H 6/7499* (2018.05); *A01H 5/08* (2013.01)

(58) Field of Classification Search
USPC ..... Plt./156, 203
See application file for complete search history.

(56) References Cited

U.S. PATENT DOCUMENTS

| | | | |
|---|---|---|---|
| PP6,679 | P | 3/1989 | Moore |
| PP6,782 | P | 5/1989 | Jennings |
| PP13,525 | P3 | 1/2003 | Fear et al. |
| PP13,758 | P3 | 5/2003 | Fear et al. |
| PP13,759 | P3 | 5/2003 | Fear et al. |
| PP14,682 | P3 | 4/2004 | Fear et al. |
| PP14,765 | P2 | 5/2004 | Cook et al. |
| PP14,780 | P2 | 5/2004 | Cook et al. |
| PP15,058 | P2 | 8/2004 | Cook et al. |
| PP17,162 | P3 | 10/2006 | Moore et al. |
| PP17,983 | P2 | 9/2007 | Cabrera |
| PP22,002 | P2 | 7/2011 | Pabon et al. |
| PP22,449 | P3 | 1/2012 | Clark |
| PP23,497 | P3 | 3/2013 | Clark et al. |
| PP23,725 | P3 | 7/2013 | Sills et al. |
| PP24,249 | P3 | 2/2014 | Clark |
| PP24,609 | P3 | 7/2014 | Rodriguez et al. |
| PP24,701 | P3 | 7/2014 | Rodriguez et al. |
| PP24,878 | P2 | 9/2014 | Alcazar et al. |
| PP25,502 | P3 | 5/2015 | Pabon et al. |
| PP26,501 | P3 | 3/2016 | Pabon et al. |
| PP26,611 | P3 | 4/2016 | Pabon et al. |
| PP26,774 | P3 | 5/2016 | Pabon et al. |
| PP27,129 | P2 | 9/2016 | Sills et al. |
| PP27,130 | P2 | 9/2016 | Sills et al. |
| PP27,146 | P2 | 9/2016 | Sills et al. |
| PP27,681 | P3 | 2/2017 | Sills et al. |
| PP27,746 | P3 | 3/2017 | Sills et al. |
| PP28,548 | P2 | 10/2017 | Sills et al. |
| PP31,110 | P2 | 11/2019 | Sills et al. |
| PP31,291 | P2 | 12/2019 | Sills et al. |
| PP31,825 | P2 | 6/2020 | Sills et al. |
| PP31,826 | P2 | 6/2020 | Sills et al. |
| PP32,268 | P2 | 10/2020 | Sills et al. |
| PP33,067 | P2 | 5/2021 | Sills et al. |
| PP33,068 | P2 | 5/2021 | Sills et al. |
| PP33,088 | P2 | 5/2021 | Sills et al. |
| PP34,069 | P2 | 3/2022 | Sills et al. |
| PP34,291 | P2 | 6/2022 | Sills et al. |
| PP34,320 | P2 | 6/2022 | Escobedo et al. |
| PP34,438 | P2 | 7/2022 | Sills et al. |
| PP34,481 | P2 | 8/2022 | Sills et al. |
| PP35,078 | P2 | 4/2023 | Sills et al. |
| PP35,233 | P2 | 6/2023 | Sills et al. |
| PP35,898 | P2 | 7/2024 | Sills et al. |
| PP36,300 | P2 | 12/2024 | Sills et al. |

OTHER PUBLICATIONS

Voss, Donald H. The Royal Horticultural Society Colour Chart 2001 Journal American Rhododendron Society, vol. 56, No. 1 2002 3 pages.

Williams, et al. DNA polymorphisms amplified by arbitrary primers are useful as genetic markers Nucleic Acids Research, vol. 18, No. 22 1990 pp. 6531-6535.

*Primary Examiner* — Karen M Redden
(74) *Attorney, Agent, or Firm* — Morrison & Foerster LLP

(57) ABSTRACT

A new and distinct variety of blackberry plant named 'DrisBlackThirtySix', particularly selected for its plant vigor, the size and firmness of fruit, and high yield potential, is disclosed.

4 Drawing Sheets

Latin name: Botanical classification: *Rubus* L. subgenus *Rubus*.

Varietal denomination: The varietal denomination of the claimed variety of blackberry plant is 'DrisBlackThirtySix'.

BACKGROUND OF THE INVENTION

Blackberry is the common name for a multitude of plant species bearing dark purple to black aggregate fruit in the genus *Rubus* of the family Rosaceae. Most blackberries are within the subgenus *Rubus*.

Native chiefly to the northern temperate regions, blackberries are now being cultivated as a valuable fruit crop in many areas of the world, particularly in Europe, North America and Central America. Recognized for their high contents of antioxidants, dietary fiber, vitamin C, and vitamin K. Blackberry fruit are typically consumed as fresh fruit, individually quick frozen fruit, or in prepared foods, such as purées, juices, jellies, jams, grocery items, baked goods, and snack foods.

Globally, Mexico is the leading producer of blackberries, with nearly the entire crop being produced for export into the off-season fresh markets in North America and Europe. The Mexican market is almost entirely from the cultivar 'Tupi'

(also spelled as 'Tupy'). In the United States, Oregon is the leading commercial blackberry producer, followed by the state of California.

Blackberries are perennial plants that typically bear biennial stems (known as "canes") from a perennial root system. The two cane types are primocanes, or first-year canes, which are usually vegetative, and floricanes, which are the same canes and produce fruit in the next growing season. In its first year, a new cane, the primocane, grows vigorously to its full length of three to six meters in a growth habit of erecting, arching, or trailing along the ground and bearing large compound leaves with 3, 5, or 7 leaflets; it does not produce any flowers. In its second year, the cane becomes a floricane and stops elongating, but the lateral buds break to produce flowering laterals that bear fruit.

Recently, primocane-fruiting blackberry varieties have been developed that are capable of flowering and fruiting on first-year canes. Primocane-fruiting blackberry varieties have several advantages, including potential of two crops on the same plant in the same year, reduction in pruning costs by mowing of canes, avoidance of winter injury, and production of fruit in an extended geographic area. However, primocane-fruiting blackberry varieties are also subject to a number of challenges, such as poor heat tolerance, lesser fruit quality, and low yield.

Blackberry is an important and valuable commercial fruit crop. Accordingly, there is a need for new varieties of blackberry plant. In particular, there is a need for improved varieties of blackberry plant that are stable, high yielding, and agronomically sound.

SUMMARY OF THE INVENTION

In order to meet these needs, the present invention is directed to an improved variety of blackberry plant. In particular, the invention relates to a new and distinct variety of blackberry plant (*Rubus* L. subgenus *Rubus*), which has been denominated as 'DrisBlackThirtySix'.

Blackberry plant variety 'DrisBlackThirtySix' was selected in Ciudad Guzmán, Mexico in April 2016 and originated from a controlled cross between the female parent proprietary blackberry plant 'BV993.8' (unpatented) and the male parent proprietary blackberry plant 'BX759.1' (unpatented). The original seedling of the new variety was first asexually propagated via root cuttings in Ciudad Guzmán, Mexico in February 2017.

'DrisBlack ThirtySix' was subsequently asexually propagated and underwent testing in Ciudad Guzmán, Mexico from 2017 to 2023 (six years). The present variety has been found to be stable and reproduce true to type through successive asexual propagations via root cuttings and tissue culture.

'DrisBlackThirtySix' was selected for its plant vigor, the size and firmness of fruit, and high yield potential.

BRIEF DESCRIPTION OF THE DRAWINGS

This new blackberry plant is illustrated by the accompanying photographs. The colors shown are as true as can be reasonably obtained by conventional photographic procedures. The photographs are of plants that are one to three years old.

DETAILED BOTANICAL DESCRIPTION

Figure 1:
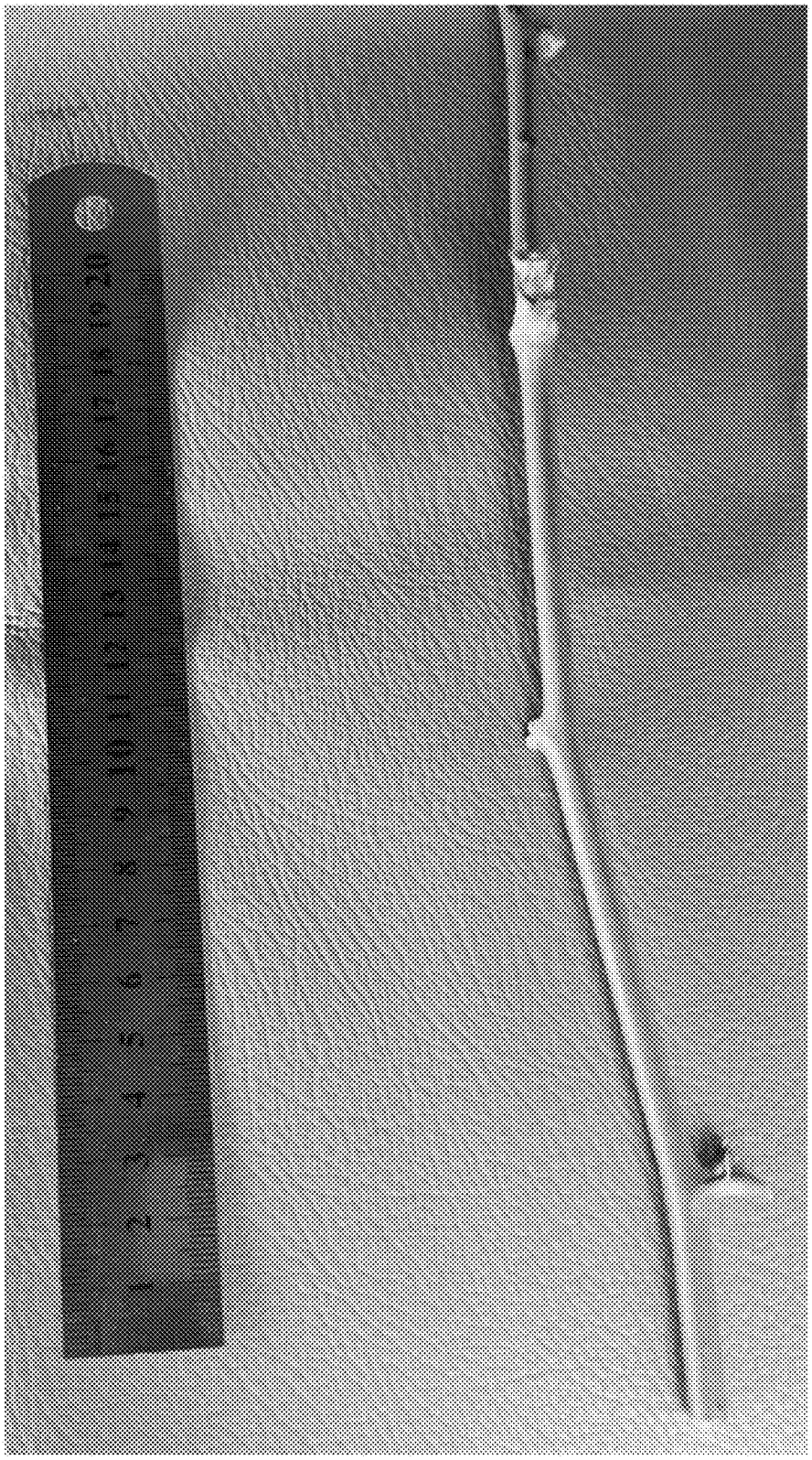
FIG. 1 illustrates a section of a cane of variety 'DrisBlackThirtySix'.
Figure 2:
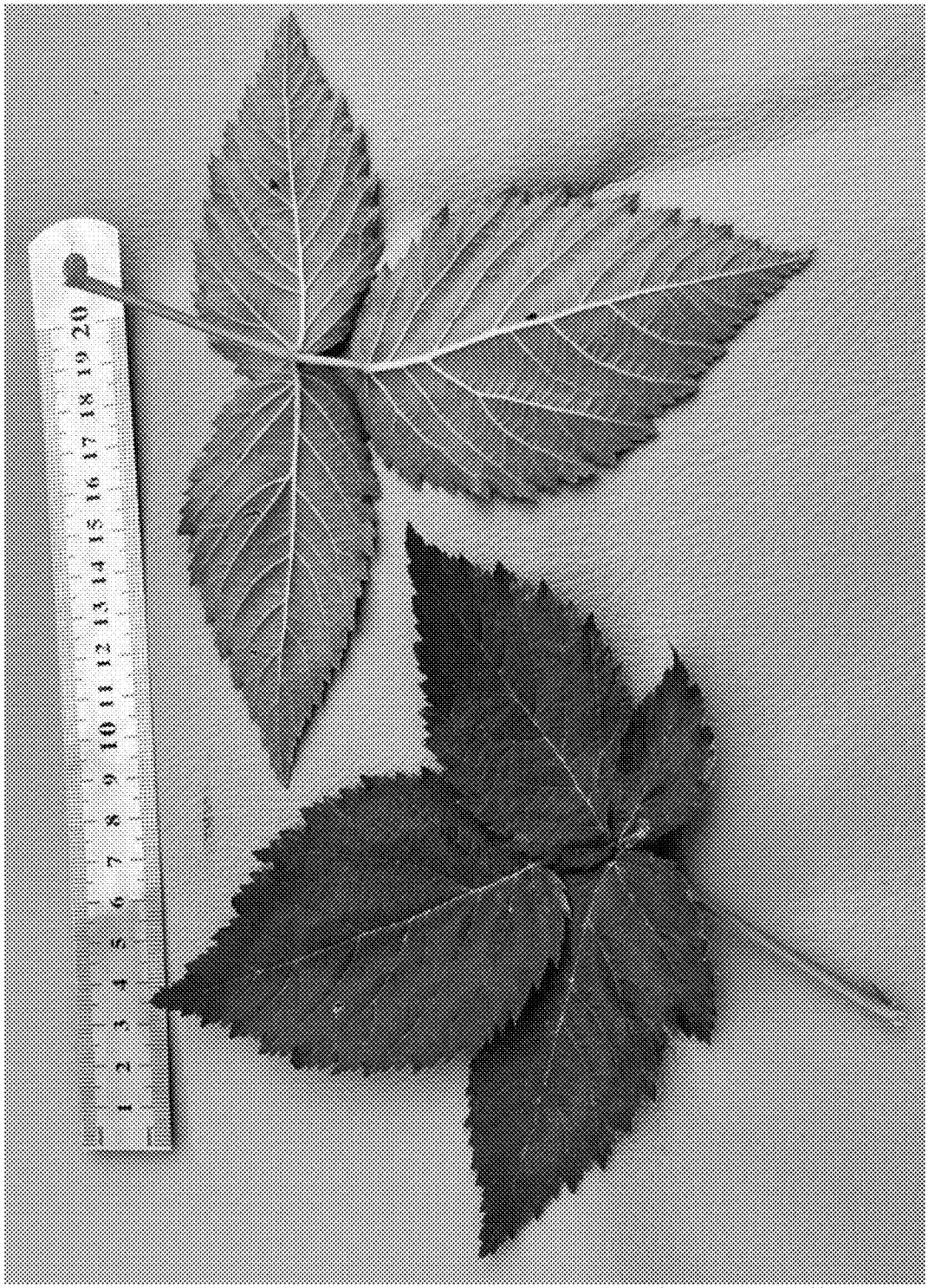
FIG. 2 illustrates the upper (left) and lower (right) surface of leaves of variety 'DrisBlackThirtySix'.
Figure 3:
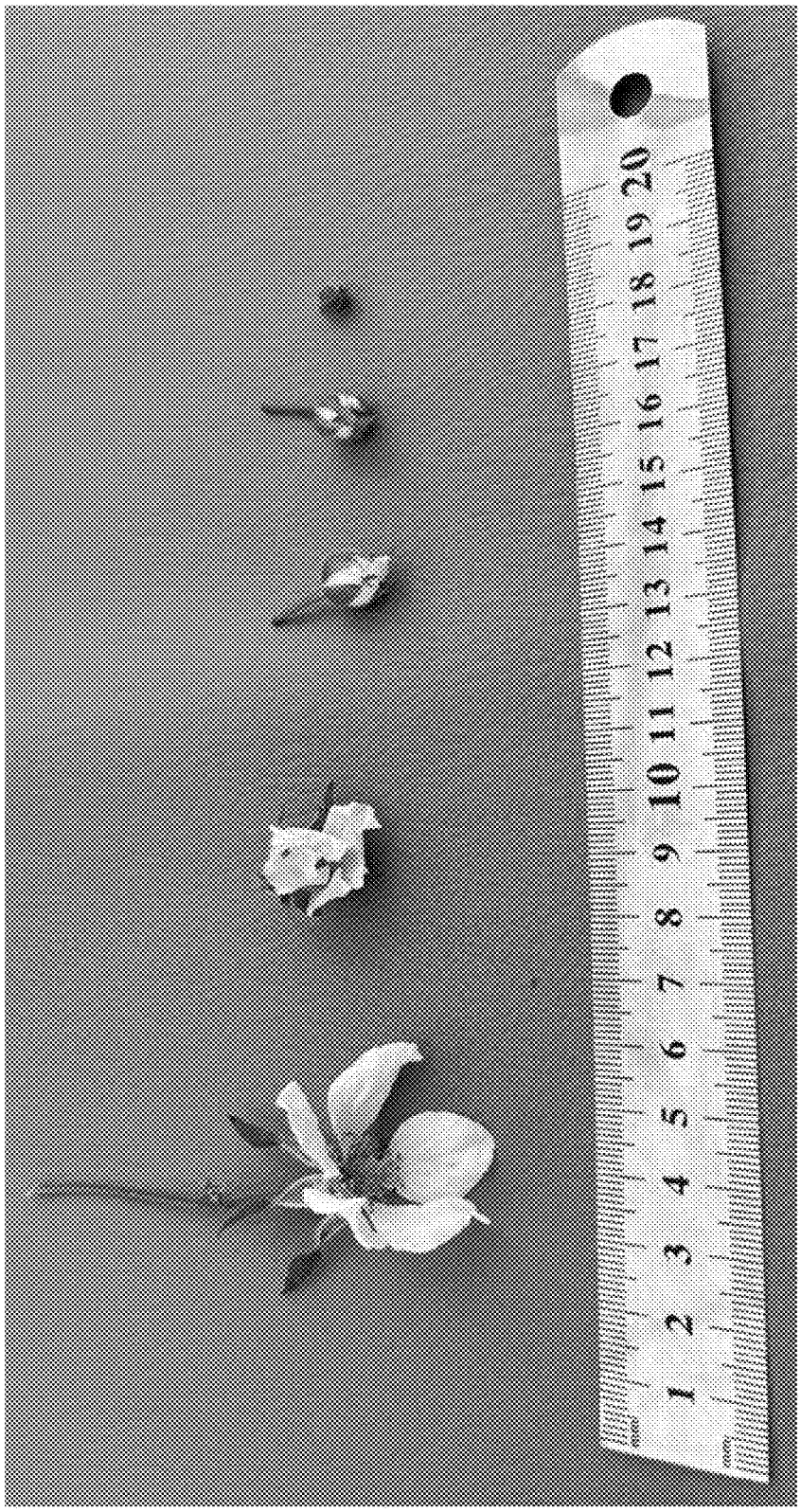
FIG. 3 illustrates flowers of varicty 'DrisBlackThirtySix' at various stages of development.
Figure 4:
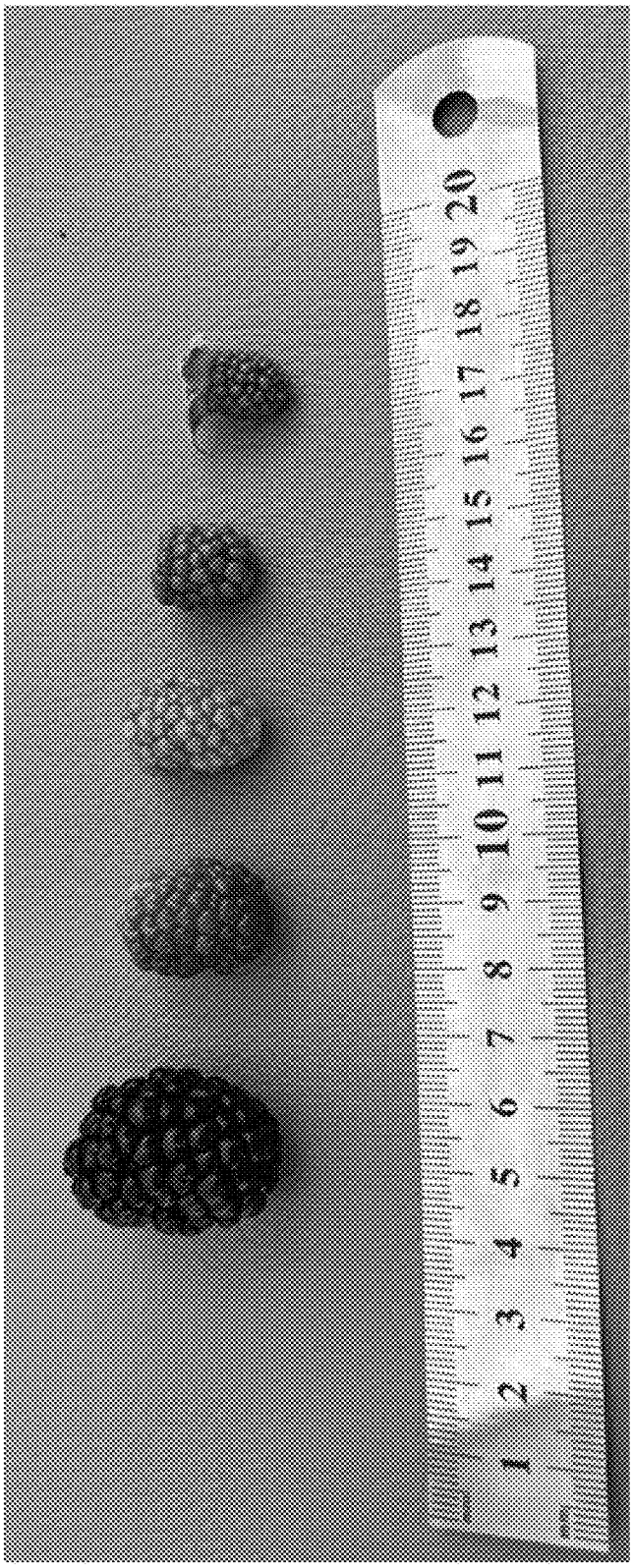
FIG. 4 illustrates fruits of variety 'DrisBlackThirtySix' at various stages of development.

The following descriptions set forth the distinctive characteristics of 'DrisBlackThirtySix'. The data that define these characteristics are based on observations taken in Ciudad Guzmán, Mexico from 2017 to 2023. This description is in accordance with UPOV terminology. Color designations, color descriptions, and other phenotypical descriptions may deviate from the stated values and descriptions depending upon variation in environmental, seasonal, climatic and cultural conditions. 'DrisBlackThirtySix' has not been observed under all possible environmental conditions. The botanical description of 'DrisBlackThirtySix' was taken from plants that were one to three years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary*, 2$^{nd}$ edition by James G. Harris and Melinda Woolf Harris, unless where otherwise defined.

Classification:

*Family*.—Rosaceae.

*Botanical*.—*Rubus* L. subgenus *Rubus*.

*Common name*.—Blackberry.

*Variety name*.—'DrisBlackThirtySix'.

Parentage:

*Female parent*.—Proprietary blackberry plant 'BV993.8' (unpatented).

*Male parent*.—Proprietary blackberry plant 'BX759.1' (unpatented).

Plant:

*Propagation*.—Root cuttings and tissue culture.

*Growth habit*.—Semi-upright.

*Vigor*.—High.

*Self-fruitfulness*.—Self-fruitful.

Canes:

*New cane*.—Number of new canes: Few. Strength: Strong. Glaucosity (waxy bloom): Weak.

*Dormant cane*.—Length: 142 cm. Diameter (in central third): 6.66 cm. Color: RHS 144A (Strong yellow green). Anthocyanin coloration: Weak. Anthocyanin coloration: RHS 46A (Strong red). Number of branches: Many. Predominant distribution of branches: Over whole length. Cross-section: Angular. Spine: Presence of spines: Absent.

*Young shoots*.—Number of young shoots: Very many. Anthocyanin coloration (during rapid growth): Weak. Anthocyanin coloration: RHS 46A (Strong red). Overall color: RHS 146B (Moderate yellow green). Number of glandular hairs: Absent or few. Time of young shoot emergence: June to October.

*Fruiting lateral*.—Length: Medium.

Leaves:

*Time of leaf bud burst*.—August to October.

*Leaf*.—Predominant number of leaflets: Five (5). Type: Palmate. Relative position of lateral leaflets: Touching. Color of upper side: RHS NN137A (Greyish olive green). Color of lower side: RHS 137D (Moderate yellowish green). Profile in cross-section: Concave (margins rolled inwards). Glossiness of upper side: Medium.

*Leaflet*.—Type of incision of margin: Bi-serrate. Depth of margin incisions: Very deep.

*Terminal leaflet*.—Length: 84.6 mm. Width: 51.4 mm. Length/width ratio: 1.64. Shape: Ovate. Apex: Retuse. Base: Obtuse. Margin: Doubly serrate. Lobing: Absent. Shape in cross-section: U-shaped. Undulation of margin: Very strong. Blistering between veins: Strong.

*Lateral leaflet*.—Length: 64.4 mm. Width: 34.9 mm. Length/width ratio: 1.84. Shape: Ovate. Base: Obtuse. Margin: Doubly serrate.

*Rachis* (*length between terminal leaflet and adjacent lateral leaflets*).—4.9 mm.

*Petiole*.—Length: 23.2 mm. Diameter: 1.6 mm.

*Stipule*.—Orientation: Reflexed.

Inflorescence:

*Flower*.—Diameter: 44.5 mm. Number of flowers observed at 3rd node from tip of lateral: 3.5.

*Petal*.—Length: 21.5 mm. Width: 9.8 mm. Length/width ratio: 2.19. Color: RHS NN155C (White).

*Flower pedicel*.—Length: 32.5 mm. Diameter: 1.37 mm.

*Flowering interval on previous year's cane* (*floricane*).—February to March.

*Flowering interval on current year's cane* (*primocane*).—August to October.

Fruit:

*Length of mature fruit*.—34.3 mm.

*Diameter of mature fruit*.—25.5 mm.

*Ratio of length to width*.—1.34.

*Fruit weight*.—8.1 g/fruit.

*Sweetness/soluble solids* (*in °Brix*).—10.2.

*Titratable acidity* (*% as citric acid*).—1.51%.

*Glossiness*.—Strong.

*Firmness*.—Firm.

*Fruit shape in longitudinal section*.—Medium ovate.

*Immature fruit color*.—RHS 143B (Strong yellow green).

*Maturing fruit color*.—RHS 179A (Moderate red).

*Mature fruit color*.—RHS 203A (Black).

*Drupe*.—Average number of drupelets per fruit: 151.

*Seed*.—Weight: 0.0035 g/seed.

*Fruiting on current year's cane*.—Present.

*Harvest interval on previous year's cane* (*floricane*).—March to May.

*Harvest interval on current year's cane* (*primocane*).—October to December.

*Yield*.—When grown in Mexico, the variety has produced up to 25 short tons of fruit per hectare per season from 6-to 12-month-old plants.

Resistance to environmental stress, pests, and diseases:

*High temperatures*.—Resistant.

*Wind*.—Resistant.

*High pH*.—Resistant.

*High soil salt levels*.—Moderately resistant.

*Waterlogging*.—Moderately susceptible.

*Two-spotted spider mite* (*Tetranychus urticae*).—Moderately resistant.

*Strawberry mite* (*Tarsonemus pallidus*).—Susceptible.

*Strawberry-blossom weevil* (*Anthonomus rubi*).—Resistant.

*Aphids* (*Aphis spp.*).—Moderately resistant.

*Lygus bug* (*Lygus hesperus*).—Resistant.

*Botrytis fruit rot* (*Botrytis cinerea*).—Resistant.

*Powdery mildew* (*Podosphaera macularis*).—Resistant.

*Verticillium wilt* (*Verticillium spp.*).—Resistant.

*Leaf scorch* (*Xylella fastidiosa*).—Moderately resistant.

*Leaf blight* (*Pseudomonas syringae*).—Resistant.

*Fusarium wilt* (*Fusarium oxysporum*).—Resistant.

COMPARISON TO PARENTAL AND REFERENCE BLACKBERRY VARIETIES

'DrisBlackThirtySix' differs from the female parent proprietary blackberry plant 'BV993.8' (unpatented) in that 'DrisBlackThirtySix' has larger fruit size and higher yield potential than 'BV993.8'.

'DrisBlackThirtySix' differs from the male parent proprietary blackberry plant 'BX759.1' (unpatented) in that 'DrisBlackThirtySix' fruit has a titratable acidity value (% as citric acid) of 1.51% and a sweetness/soluble solids value (in °Brix) of 10.2, whereas 'BX759.1' fruit has a titratable acidity value (% as citric acid) of 1.81% and a sweetness/soluble solids value (in °Brix) of 9.6. 'DrisBlackThirtySix' fruit thus has lower acidity and higher sweetness as compared to 'BX759.1', which results in a different flavor profile as compared to 'BX759.1'.

'DrisBlackThirtySix' differs from the reference variety 'DrisBlackThirteen' (U.S. Plant Pat. No. 27,681) in that 'DrisBlackThirtySix' has weak anthocyanin coloration on dormant cane, very strong undulation of margin on terminal leaflets, white petal color, and strong fruit glossiness, whereas 'DrisBlackThirteen' has medium anthocyanin coloration on dormant cane, absent or very weak to weak undulation of margin on terminal leaflets, the petal color is white with violet tinge, and weak to medium fruit glossiness.

'DrisBlackThirtySix' differs from the reference variety 'DrisBlackTwentySix' (U.S. Plant Pat. No. 34,320) in that 'DrisBlackThirtySix' has weak anthocyanin coloration on dormant cane, spines absent on dormant cane, very strong undulation of margin on terminal leaflets, and medium ovate shape of fruit in longitudinal section, whereas 'DrisBlackTwentySix' has absent or very weak anthocyanin coloration on dormant cane, spines present on dormant cane, absent or very weak undulation of margin on terminal leaflets, and long conical shape of fruit in longitudinal section.

What is claimed is:

1. A new and distinct variety of blackberry plant designated 'DrisBlackThirtySix' as shown and described herein.

* * * * *